United States Patent [19]

Holland

[11] 4,430,337

[45] Feb. 7, 1984

[54] ALICYCLIC SUBSTITUTED OXAZOLIDINE-2,4-DIONES HAVING HYPOGLYCEMIC ACTIVITY

[75] Inventor: Gerald F. Holland, Old Lyme, Conn.

[73] Assignee: Pfizer Inc., New York, N.Y.

[21] Appl. No.: 391,220

[22] Filed: Jun. 23, 1982

[51] Int. Cl.³ .................... C07D 263/44; A61K 31/42
[52] U.S. Cl. ................................. 424/272; 548/226; 548/227; 568/308
[58] Field of Search ................. 548/227; 424/272

[56] References Cited

U.S. PATENT DOCUMENTS

| | | | |
|---|---|---|---|
| 2,338,064 | 12/1943 | Stoughton | 548/226 |
| 2,349,313 | 5/1944 | Stoughton | 548/226 |
| 2,349,795 | 5/1944 | Stoughton | 548/226 |
| 2,349,796 | 5/1944 | Stoughton | 548/226 |
| 2,575,692 | 11/1951 | Spielman | 548/226 |
| 2,575,693 | 11/1951 | Spielman | 548/226 |
| 2,575,694 | 11/1951 | Spielman | 548/226 |
| 2,961,377 | 11/1960 | Shapiro et al. | 548/226 |
| 4,200,642 | 4/1980 | Schnur | 548/226 |
| 4,332,952 | 6/1982 | Schnur | 548/226 |
| 4,367,234 | 1/1983 | Schnur | 548/226 |

FOREIGN PATENT DOCUMENTS 226529  12/1957  United Kingdom ............... 548/226

Primary Examiner—Donald G. Daus
Assistant Examiner—S. A. Gibson
Attorney, Agent, or Firm—Charles J. Knuth; Albert E. Frost; Robert K. Blackwood

[57] ABSTRACT

Hypoglycemic oxazolidine-2,4-diones, substituted at the 5-position with a ($C_5$–$C_9$) unsaturated monocyclic, saturated bicyclic or unsaturated bicyclic hydrocarbon radical; methods for their preparation; and method for their use in the treatment of hyperglycemic mammals.

23 Claims, No Drawings

ALICYCLIC SUBSTITUTED OXAZOLIDINE-2,4-DIONES HAVING HYPOGLYCEMIC ACTIVITY

BACKGROUND OF THE INVENTION

The present invention relates to certain novel oxazolidine-2,4-diones substituted at the 5-position with an unsaturated cyclic, a saturated bicyclic or an unsaturated bicyclic radical of the formula $C_nH_{2n-3}$ or $C_nH_{2n-5}$ wherein n is an integer of value 5-9. These compounds possess hypoglycemic activity and so are useful in reducing the level of glucose in a hyperglycemic mammal, including man.

In spite of the early discovery of insulin and its subsequent wide-spread use in the treatment of diabetes, and the later discovery and use of sulfonylureas (e.g., chlorpropamide, tolbutamide, acetohexamide, tolazamide) and biguanides (e.g. phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Where effective, a synthetic hypoglycemic agent is preferred over insulin, being more convenient to administer and less prone to cause severe hypoglycemic reactions. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057-1080]. Most recently, oxazolidine-2,4-diones substituted at the 5-position with various aromatic and heteroaromatic groups have been described as having hypoglycemic activity. (Schnur, Belgian Pat. Nos. 889,757 and 889,758, both publicly available Jan. 28, 1982).

The oxazolidine-2,4-diones of the present invention are novel, in spite of the fact that the oxazolidine-2,4-diones are broadly known as a class of compounds [for an extensive review, see Clark-Lewis, Chem. Rev. 58, pp. 63-99 (1958)]. Among the compounds known in this class are 5-phenyloxazolidine-2,4-dione, variously reported as an intermediate to certain beta-lactam antibacterial agents (Sheehan, U.S. Pat. No. 2,721,197), as an antidepressant agent (Plotnikoff, U.S. Pat. No. 3,699,229), as an anticonvulsant agent [Brink and Freeman, J. Neuro. Chem. 19 (7), pp. 1783-1799 (1972)], and as a hypoglycemic agent (Schnur, loc. cit.).

Oxazolidine-2,4-dione and substituted oxazolidine-2,4-diones (specifically, the 5-methyl and 5,5-dimethyl derivatives) have been reported as acid moieties suitable for forming acid-addition salts with the hypoglycemic, basic biguanides (Shapiro and Freedman, U.S. Pat. No. 2,961,377). We have determined that neither oxazolidine-2,4-dione itself, nor 5,5-dimethyloxazolidine-2,4-dione possess the hypoglycemic activity of the compounds of the present invention.

Recently, a group of spiro-oxazolidine-2,4-dione derivatives have been reported which are aldose reductase inhibitors, thus finding utility in the treatment of certain complications of diabetes (Schnur, U.S. Pat. No. 4,200,642).

SUMMARY OF THE INVENTION

In view of the inactivity of oxazolidine-2,4-dione and 5,5-dimethyloxazolidine-2,4-dione, and the fact that in the 5-phenyl substituted oxazolidine-2,4-dione series, certain ortho-alkoxy and halo derivatives are much preferred, we have surprisingly found that certain simple, unsubstituted alicyclic oxazolidine-2,4-diones are potent hypoglycemic agents, and therefore of special value in lowering the level of blood sugar in hyperglycemic mammals.

The oxazolidine-2,4-dione compounds of the present invention are of the formula

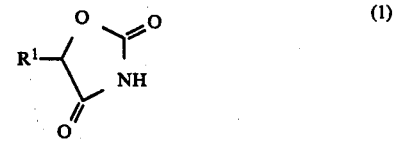

or a pharmaceutically-acceptable cationic salt thereof; wherein $R^1$ is a hydrocarbon radical having a molecular formula which is either $C_nH_{2n-3}$ or $C_nH_{2n-5}$, wherein n is an integer of value 5 to 9, which is further characterized by having within its structure:

(a) at least one and up to two carbocyclic rings, with at least one of said rings comprising five or more carbon atoms;

(b) up to one carbon-carbon double bond; and (c) up to one substituent $(C_1-C_3)$alkyl or $(C_1-C_3)$alkylidene group.

Because of their excellent hypoglycemic activity and ease of preparation from available starting materials, preferred compounds of the present invention are defined as follows:

(a) When $R^1$ is $C_nH_{2n-5}$ (unsaturated bicyclic) preferred compounds are endo- or exo-5-(bicyclo[2.2.1]-hept-5-en-2-yl)oxazolidine-2,4-dione (most preferably the endo- form thereof, viz.,

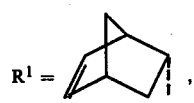

and 5-(Bicyclo[3.1.0]hex-2-en-6-yl)oxazolidine-2,4-dione, viz.,

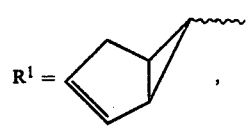

(b) When $R^1$ is $C_nH_{2n-3}$ (saturated bicyclic) preferred compounds are endo- or exo-5-(bicyclo[2.2.1]-hept-2-yl)oxazolidine-2,4-dione (most preferably the endo- form thereof) and 5-(bicyclo[3.1.0]hex-6-yl)oxazolidine-2,4-dione.

(c) When $R^1$ is $C_nH_{2n-3}$ (unsaturated monocyclic), the preferred compounds are 3-cyclohexen-1-yl derivatives, unsubstituted or substituted with a methyl or an ethyl group at the 2-, 4- or 6-position, the methyl sustituent being somewhat preferred over the ethyl substituent. Most preferred are the 2-methyl- and 2-ethyl-3-cyclohexen-1-yl derivatives having 1,2-cis-hydrogens on the cyclohexene ring, in particular 5R*(2S*-methyl-3-cyclohexen-1R*-yl)oxazolidine-2,4-dione, i.e. the racemic compound having the relative stereochemical formula

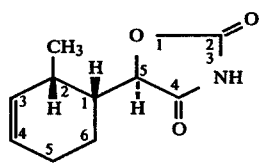   (2)

which is herein called as the cis-I isomer.

The expression "pharmaceutically acceptable cationic salts" is intended to define such salts as the alkali metal salts, (e.g., sodium and postassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine.

DETAILS OF THE INVENTION

The compounds of the present invention are prepared by a variety of methods, as summarized in Flowsheet I, wherein $R^1$ is as defined above;
$R^2$ is lower alkyl (e.g. methyl or ethyl);
$R^3$ is hydrogen, lower alkyl or phenyl; and
$R^4$ is hydrogen, or acyl such as acetyl or benzoyl.

Particularly suitable precursors for the oxazolidine-2,4-diones of the present invention are the alpha-hydroxy amides (5). The latter compound is converted to the desired oxazolidine-2,4-dione (1) either by reaction with alkyl chloroformate in the presence of a basic catalyst such as potassium carbonate, Flowsheet I
Oxazolidine-2,4-dione Precursors

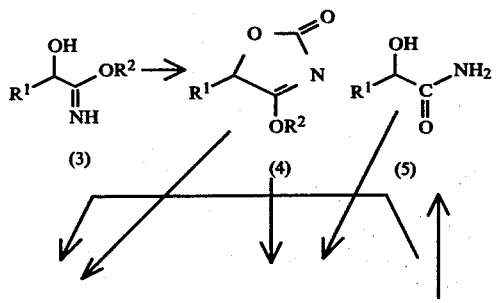

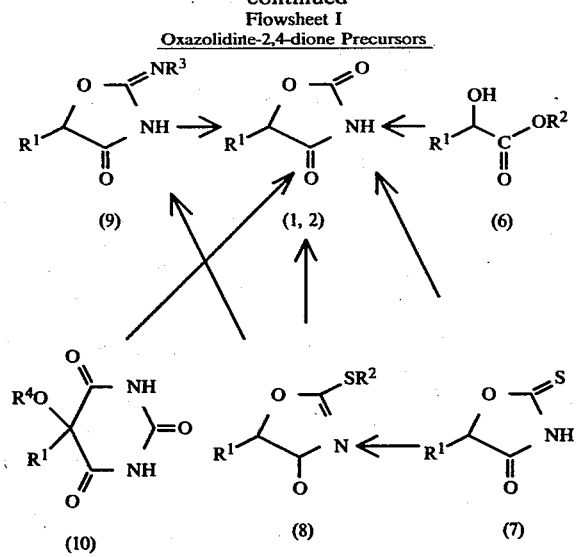

or by reaction with a dialkyl carbonate in the presence of a more strongly basic catalyst such as sodium methoxide or potassium tert-butoxide. An alcohol is generally suitable as solvent for the latter reaction with 1 to 10 equivalents of both dialkyl carbonate and base employed, preferably 3-10 equivalents of dimethyl carbonate and 3-5 equivalents of a sodium methoxide in ethanol as solvent. Temperature is not critical, and is conveniently in the range 50°-100° C., most conveniently at the reflux temperature of the alcohol used as solvent.

The required alpha-hydroxy amide is conveniently prepared from cyanohydrin (11) or from alpha-hydroxy acid or ester (6):

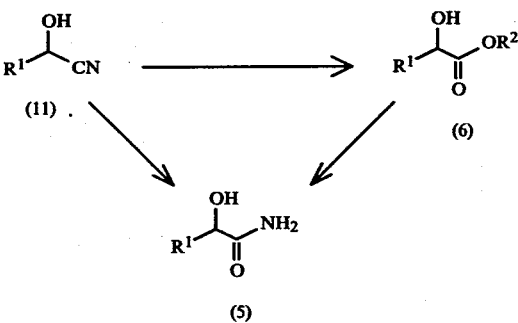

Convenient conditions for the hydrolysis of the cyanohydrin (11) are to treat the cyanohydrin with a little more than an equivalent of potassium hydroxide and a large excess of 30% hydrogen peroxide in an aqueous solvent, suitably aqueous ethanol. The reaction mixture is carefully heated to the point of reflux. Heat is removed, and reflux allowed to proceed. Once reflux ceases, heat is again applied and reflux is continued for 15-30 minutes prior to isolation of amide (5) by standard techniques of concentration and extraction. Alternatively cyanohydrin (11) is converted to amide (5) with excess aqueous hydrochloric acid, preferably in the presence of a water miscible, reaction-inert organic solvent such as dioxane at −5° to 30° C.

The required 2-hydroxyacetonitriles (cyanohydrins) are generally derived from the corresponding aldehydes, usually via the bisulfite adduct, which is reacted with cyanide in an aqueous or aqueous organic solvent.

The required aldehydes, in turn, are available commercially or by literature methods such as Rosenmund reduction of corresponding acid chloride, from corresponding halomethyl compounds via the Sommelet reaction, oxidation of corresponding hydroxymethyl compounds or condensation reactions as exemplified below.

A second convenient synthesis for compounds of the present invention is via carboximidate (3). The latter compound is reacted with phosgene in an inert solvent such as tetrahydrofuran in the presence of 2 to 2.3 equivalents of a tertiary amine (e.g. triethylamine, N-methylmorpholine). A further equivalent of tertiary amine is used if the carboximidate is introduced as the acid addition salt (e.g. hydrochloride salt). The temperature of the reaction is not critical, but lower temperatures (e.g. $-10°$ to $10°$ C.) are preferred during the initial stages of the reaction, particularly if it is desired to isolate the intermediate 4-alkoxyoxazol-2-one (4). Isolation of this intermediate is carried out by simple evaporation of the reaction mixture to dryness. On further reaction at higher temperatures (e.g. $20°-50°$ C.) or on aqueous work-up the intermediate (4) is converted to the desired oxazolidine-2,4-dione.

The alternative carboximidate precursors (3) are also conveniently prepared from the corresponding aldehyde via cyanohydrin (11) or via the trimethylsilyl cyanohydrin:

(12)

The aldehyde is converted to the trimethylsilyl cyanohydrin (12) by reaction with trimethylsilylcarbonitrile in the presence of a catalytic quantity of a Lewis acid, e.g., zinc iodide. A reaction inert solvent (e.g. methylene chloride, ether) is generally used when the aldehyde is a solid, but is optional when the aldehyde is a liquid. The temperature of the reaction is not critical, it being conveniently made up at reduced temperature (e.g. $0°-5°$ C.) and allowed to proceed at room temperature for a matter of hours or days, as necessary to achieve complete reaction. If desired, the trimethylsilyl ether can be hydrolyzed to cyanohydrin, conveniently at reduced temperature (e.g. $-10°$ C.) in a two phase strong aqueous acid/organic solvent system.

Either the cyanohydrin (11) or the trimethylsilyl ether (12) is converted to the carboximidate (3) by strong acid catalyzed alcoholysis (using strictly anhydrous conditions). A convenient method is to simply dissolve the nitrile in alcohol which has been saturated with hydrogen chloride) and allow the solution to stand until carboximidate formation is complete. Temperature is not critical, although lower temperatures (e.g. $0°-25°$ C.) generally lead to more optimal yields.

The alpha-hydroxy ester (6) itself can also be employed as the immediate precursor of the desired oxazolidine-2,4-dione. The ester is reacted with urea (or one of certain substituted ureas, such as phenyl urea or 1-acetyl-3-methylurea) in the presence of a basic catalyst such as sodium ethoxide (suitably 1 equivalent) in alcohol at a temperature of $50°-110°$ C. The ester to be used for this purpose is by no means restricted to a simple lower alkyl ester, but can be any one of a broad variety of esters, e.g. phenyl, benzyl, etc. Furthermore, the ester can be replaced by a 1,3-dioxolan-4-one, e.g.,

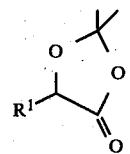

and the urea can be replaced by a urethan.

Two other precursors suitable for the synthesis of the desired oxazolidine-2,4-diones are the thio compounds (7) and (8). The 2-thioxo compound (7) is converted to the desired oxazolidine-2,4-diones under oxidative conditions, e.g. mercuric ion, aqueous bromine or chlorine, or aqueous hydrogen peroxide, usually in excess and in the presence of a co-solvent, such as a lower alcohol. The temperature of reaction is not critical, temperatures in the range $25°-100°$ C. generally satisfactory. The oxazolidine-2,4-diones are obtained from the alkylthio compounds (8) by simple acid or base catalyzed hydrolysis. Preferable conditions are aqueous hydrochloric acid in a temperature range of $0°-50°$ C.

The precursor 2-thioxo compound (7) is also prepared from the corresponding aldehyde, generally accomplished in an aqueous acidic media by the action of thiocyanate (1–1.1 equivalents) and cyanide (1 to 1.2 equivalents) at $0°-70°$ C., following the method of Lindberg and Pederson by which method the preparation of 5-(2-thienyl)-2-thioxooxazolidin-4-one has been reported [Acta Pharm. Suecica 5 (1), pp. 15–22 (1968); Chem. Abstr. 69, 52050k]. The precursor 2-alkylthio compounds (8) can be prepared by alkylation of the 2-thioxo compounds (7), e.g. with an alkyl halide or dialkyl sulfate, preferably in the presence of at least two equivalents of a base such as alkoxide in a reaction inert solvent such as an alkanol. The 3-alkyl derivative can be a by-product of this reaction.

Also suitable as a precuror is the 2-iminooxazolidine-4-one derivative (9), readily hydrolyzed to the oxazolidine-2,4-dione, preferably under aqueous acid conditions. The required 2-iminooxazolidin-4-one is obtained by condensation of the alpha-hydroxy ester (6) with guanidine or with thiourea in the presence of one equivalent of a strong base such as sodium alkoxide, by ammonolysis of the 2-alkoxy compound (isomeric with 4) or the 2-thioalkyl compound (8), by alkali induced cyclization of the appropriate alpha-halogenureides ($R^1CHZCONHCONHR^3$ wherein Z is a halogen such as chloro or bromo), or by the condensation of the appropriate alkyl alpha-haloacetates ($R^1CHZCOOR^2$) with urea or a substituted urea ($R^3NHCONH_2$).

Ammonolysis of the 4-alkoxy derivatives (4) yields 4-imino derivatives (isomeric with 9). The latter compounds are also readily hydrolyzed to oxazolidine-2,4-diones. The 4-alkoxy derivatives themselves are also prepared from the silver salt of the desired oxazolidine-2,4-dione.

Also highly useful as precursors of the oxazolidine-2,4-diones of the present invention are the dialuric acids and acyl dialuric acids (10). These are readily converted, under mildly basic conditions, to the desired oxazolidine-2,4-diones. Methods suitable for the preparation of precursor dialuric acids (10) are shown in Flowsheet II, wherein the substituents $R^1$, $R^2$ and $R^4$ are as defined above, and M is Li, MgCl, MgBr, MgI, or other suitable metal.

A general method for preparing dialuric acids appropriate as precursors of the oxazolidine-2,4-diones of the present invention is from the malonic ester derivatives (14), involving the two stages of base catalyzed condensation with urea and oxidation to the hydroxy or acyloxy compound. When the first stage is oxidation, the intermediate is a so-called tartronic acid derivative (15), while when the first stage is condensation, the intermediate is a so-called barbituric acid (16). When condensation is the second stage, the dialuric acid is usually not isolated, at least in pure form, and is further converted, under the basic conditions of the condensation, to the oxazolidine-2,4-dione.

The substituted malonic esters required for the above syntheses, when not available commercially, are obtained by literature methods, such as alcoholysis of alpha-cyano esters [cf. Steele, J. Am. Chem. Soc. 53, 286 (1931)], carbalkoxylation of esters [cf. Horning and Finelli, Org. Syntheses 30, 43 (1950)] and decarbonylation of alpha-keto esters obtained by the condensation of dialkyl oxalate with carboxylate esters [Reichstein and Morsman, Helv. Chim. Acta 17, 1123 (1934); Blicke and Zienty, J. Am. Chem. Soc. 63, 2946 (1941)],

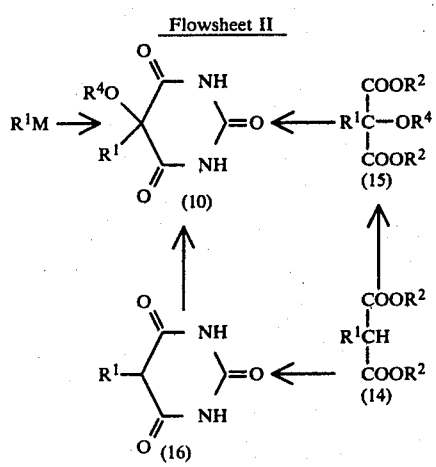

Flowsheet II

Now available is yet another broadly applicable method, preferred when the appropriate starting materials are readily available, which involves the reaction of alloxan (preferably in anhydrous form) with the appropriate organometal derivative (e.g. organolithium, Grignard reagent, $R^1M$, $M=Li$ or $MgX$, $X=Cl$, Br or I). The required organometal reagents are derived from the corresponding alicyclic halide ($R^1X$). The latter are available commercially or by literature methods.

It will be evident to those skilled in the art that the preferred process for the oxazolidine-2,4-diones of the present invention will vary from one given value of $R^1$ to another, depending upon such factors as availability of starting materials, yields, ability to remove undesirable impurities from the endproducts, the chemical nature of the substituent groups contained in the final products, etc.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and/or addition of a non-solvent.

The saturated bicyclic compounds of the present invention are also conveniently synthesized by hydrogenation of a corresponding unsaturated bicyclic compounds of the present invention. These hydrogenations are generally carried out under a hydrogen atmosphere, in a reaction-inert solvent in the presence of a suitable homogeneous or heterogeneous noble metal catalyst. As used herein, reaction-inert solvent refers to a medium which is a suitable solvent or suspending agent and which does not react with starting materials, products, intermediates or reagents in such a manner as to significantly reduce the yield of the desired product. Polar organic solvents are generally suited to the present hydrogenations and include water, ($C_1-C_5$)alcohols, ethers (such as tetrahydrofuran and 1,2-dimethoxyethane) and ether-alcohols (such as 2-methoxyethanol) or combinations thereof. Ethanol is a preferred solvent in the present instance. Temperature is not critical and is conveniently in the range 0°–100° C., most conveniently 20°–30° C. Pressure is likewise not critical; pressures in the range from subatmospheric to 150 atmospheres or greater are suitable. Preferred are moderate pressures such as 1 to 7 atmospheres. The noble metal catalysts here employed include platinum, palladium, rhodium and ruthenium, either of the heterogeneous supported type (e.g. on carbon, barium sulfate, alumina) or non-supported type, as well as known catalytic compounds thereof such as the oxides and chlorides; or of the homogeneous type such as rhodium chloride tris-(triphenylphosphine), so-called Wilkinson catalyst. A particularly convenient catalyst for the present purpose is 5% Pd/C, conveniently used at ambient temperature and low pressure (3–4 atmospheres).

The reactions employed to prepare the compounds of this invention can generally be monitored by standard tlc methods, employing commercially available plates. Suitable eluants, which are common solvents such as chloroform, ethyl acetate or hexane or combinations thereof, optionally in the presence of a minor portion of an organic acid (e.g. 5% acetic acid), are readily devised to differentiate starting materials, products, by-products, and in some cases intermediates. Application of these methods, which are well known in the art, will permit further improvement in the methodology of the specific examples detailed hereinafter, e.g. the selection of more optimal reaction times and temperatures, as well as aid in the selection of optimal processes.

The oxazolidine-2,4-diones of the present invention are readily adapted to clinical use as antidiabetic agents. The hypoglycemic activity required for this clinical use is defined by the glucose tolerance test procedure which follows. Intact male albino rats are the experimental test animals employed for such purposes. The test animals are fasted approximately 18–24 hours. The rats are weighed, numbered and recorded in groups of five or six as needed. Each group of animals is then dosed intraperitoneally with glucose (one gram per kilogram) and orally with either water (controls) or compound (at a level usually selected from the range 0.1 to 100 mg./kg.). Blood glucose levels (mg./100 ml.) are measured in tail blood samples over a period of 3 hours in both control and treated groups. With equivalent zero hour blood glucose levels in control and treated groups, the % lowering of blood glucose at 0.5 hour, 1 hour, 2 hours and 3 hours is calculated as:

$$\frac{[\text{Control Blood Glucose}] - [\text{Treated Blood Glucose}]}{[\text{Control Blood Glucose}]} \times 100\%$$

Clinically useful hypoglycemic agents show activity in this test. The hypoglycemic activities determined for representative compounds of the present invention are summarized in Table I. This table records the maximum % blood glucose lowering noted over the 3 hour observation period, usually at the 0.5 hour and 1 hour time points. A blood glucose lowering of 9% or greater generally reflects statistically significant hypoglycemic activity in this test.

The oxazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.20 to about 20 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

TABLE I

Hypoglycemic Activity of Oxazolidine-2,4-Diones of the Formula (1)

| $R^1$ | Oral Dose (mg/kg) | Maximum % Lowering Blood Glucose 0.5–3 hours |
|---|---|---|
| bicyclo[2.2.1]hept-5-en-2-yl | | |
| mixed endo- and exo- | 25 | 17 |
| endo- | 25 | 23 |
| endo-bicyclo[2.2.1]hept-2-yl | 25 | 26 |
| bicyclo[3.1.0]hex-2-en-6-yl | 25 | 22 |
| 1-methyl-3-cyclohexen-1-yl | 25 | 9 |
| 6-methyl-3-cyclohexen-1-yl | 25 | 24 |
| 2-methyl-3-cyclohexen-1-yl | | |
| mixed isomers | 25 | 27 |
| cis-I isomer | 5 | 23 |
| 2-ethyl-3-cyclohexen-1-yl | | |
| mixed isomers | 25 | 29 |
| cis-I isomer | 5 | 17 |

The compounds can be used in pharmaceutical preparations containing the compound, or a pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions can, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

It will be evident to those skilled in the art that the compounds of the present invention are asymmetric and therefore capable of existing in two optically active enantiomeric forms. The racemic compounds of the present invention, being acids, form salts with organic amines. These racemic forms are therefore generally capable of resolution into the optically active forms by the classic method of forming diastereomeric salts with optically active amines, now separable by selective crystallization. In general, one of the enantiomeric forms is found to have greater activity than the other.

The present invention is illustrated by the following examples. However, it should be understood that the invention is not limited to the specific details of these examples. Pnmr (proton nuclear magnetic resonance)-spectra were determined in CDCl$_3$ at 60 MHz with TMS standard.

EXAMPLE 1

Trans-2-(2-Methyl-3-cyclohexen-1-yl)-2-hydroxyacetonitrile

Sodium bisulfite (10.4 g., 0.1 mole) was dissolved in 50 ml. H$_2$O. Absolute ethanol (50 ml.) and trans-2-methyl-3-cyclohexene-1-carbaldehyde (85%, 8.6 g., 0.07 mole) were added and the mixture heated in an oil bath at 63°–65° C. for 1.5 hours, then cooled to 15° C. in an ice-water bath. KCN (13 g., 0.2 mole) in 50 ml. H$_2$O was added at 15°–18° C. The reaction mixture was stirred at room temperature 0.5 hour and extracted with 150 ml. ether. The ether was back-washed with 75 ml. H$_2$O and concentrated in vacuo to yield title product as an oil, 5.5 g. Based on pnmr, the product contained 85% trans isomer (doublet at 4.6 ppm, J=4) and 15% cis isomer (doublets at 4.2 and 4.35, J=2).

EXAMPLE 2 cis-2-(2-Methyl-3-cyclohexen-1-yl)-2-hydroxyacetonitrile

By the method of the preceding Example, cis-2-methyl-3-cyclohexene-1-carbaldehyde (85%, 8.6 g.) was converted to 7.9 g. of title product containing 80% cis isomer by pnmr assay.

EXAMPLE 3 cis-2-(2-Methyl-3-cyclohexen-1-yl)-2-hydroxyacetamide

Title product of the preceding Example (7.8 g., 0.052 mole), ethanol (75 ml.), KOH (85%, 3.8 g., 0.057 mole) and 30% $H_2O_2$ (150 ml., 1.5 mole) were combined and heated carefully to reflux. The oil bath was removed and reflux allowed to proceed. After reflux ceased, the oil bath was restored and reflux continued for 15 minutes, by which time starch-KI test paper was negative for peroxides. $NaHSO_3$ (about 1 g.) was added and the mixture concentrated in vacuo to a syrup. $H_2O$ (25 ml.) was added and the partially crystallized material extracted with 75 ml. ethyl acetate. The organic layer was back-washed with 15 ml. $H_2O$, dried over $Na_2SO_4$ and concentrated to in vacuo to yield title product as an oil [2 g., pnmr indicates the presence of some trans isomer; Rf 0.1 (hexane:ethyl acetate 5:1/5% acetic acid)].

EXAMPLE 4 trans-2-(2-Methyl-3-cyclohexen-1-yl)-2-hydroxyacetamide

By the method of the preceding Example, the title product of Example 1 (85%, 5.5 g.) was converted to present title product, except that the final organic layer was evaporated to 15 ml. and pure title product crystallized by the addition of 10 ml. of water [770 mg., m.p. 149°–151° C.; Rf 0.2 (hexane:ethyl acetate 5:1/5% acetic acid); only trans isomer by pnmr)].

EXAMPLE 5 trans-5-(2-Methyl-3-cyclohexen-1-yl)-oxazolidine-2,4-dione (Trans-I and Trans-II Isomers)

Title amide of the preceding Example (1 g., 6 mmoles), absolute ethanol (75 ml.), sodium methoxide (1.6 g., 0.03 mole) and diethyl carbonate (7.5 ml., 0.06 mole) were combined and refluxed 1.5 hours under $N_2$. The reaction mixture was stripped to dryness and the residue taken up in 25 ml. $H_2O$. The basic solution was extracted with 20 ml. ether, acidified with 6N HCl and diluted with 10 ml. hexane. The precipitated oil, a mixture of title isomers I and II, crystallized on stirring the mixture for 15 minutes at room temperature, 1 g., m.p. 97°–103° C. The mixed crystals were recrystallized from ether-hexane to yield title isomer I, 374 mg., containing 3% title isomer II, m.p. 109°–115° C. A second recrystallization from ether-hexane gave analytically pure title isomer I, 160 mg., m.p. 111°–113° C.

Anal. Calcd. for $C_{10}H_{13}O_3N$: C, 61.52; H, 6.71; N, 7.18; O, 24.59. Found: C, 61.64; H, 6.61; N, 7.11; O, 24.51.

Recrystallization mother liquors were evaporated to dryness. Residue (500 mg.) was chromatographed on 50 ml. of silica gel, using 2:1 hexane:ethyl acetate as eluant, monitoring by pnmr. Only partial separation of isomers was indicated. Fractions enriched in isomer II combined with additional mother liquor residue (700 mg. total) was further chromatographed on 70 ml. silica gel, now using 5:1 hexane:ethyl acetate as eluant and collecting 8 ml. fractions. Fractions 23–26 containing primarily the desired title isomer II were evaporated to solids (160 mg.) and recrystallized from ether hexane to yield purified title isomer II in two crops, 43 mg., m.p. 93.5°–94.5 °C.

Anal. Calcd. for $C_{10}H_{13}O_3N$: C, 61.52; H, 6.71; N, 7.18. Found: C, 61.83; H, 6.68; N, 7.46.

Although it is known that in the title isomers I and II that the 1,2-ring hydrogens are trans, the full relative stereochemistry of these two racemic compounds has not been established.

EXAMPLE 6

5R*-(2S*-Methyl-3-cyclohexen-1R*-yl)oxazolidine-2,4-dione (cis-I Isomer)

and

5S*-(2S*-Methyl-3-cyclohexen-1R*-yl)oxazolidine-2,4-dione (cis-II Isomer)

Title amide of Example 3 (3 g.) was converted to crude cis-I and II isomers according to the procedure of the preceding example, except that no hexane was added to the acidified aqueous layer in isolation; rather product was extracted into 2×150 ml. ethyl acetate, which was backwashed with 50 ml. of water and evaporated to a brown oil, 2.6 g. The oil was column chromatographed on 120 ml. silica gel with 1:1 hexane: ethyl acetate as eluant to produce a purified mixture of title isomers (1.7 g.). The purified mixture was dissolved in 3 ml. of ether and 15 ml. hexane added. On standing there crystallized a crop containing about 90% title cis I isomer (300 mg.) which on recrystallization from 1:2 ether hexane gave purified title cis-I isomer, 85 mg., m.p. 133°–135° C., pnmr includes doublet at 4.55 and 4.70 (J=10).

Anal. Calcd. for $C_{10}H_{13}O_3N$: C, 61.52; H, 6.71; N, 7.18. Found: C, 61.38; H, 6.60; N, 7.04.

From the mother liquor of the 90% cis-I isomer, a second crop crystallized, 295 mg., m.p. 86°–88° C., about 90% title cis-II isomer by pnmr (4.85 ppm, d, J=5.3). Recrystallization from 1 ml. ether and 3 ml. hexane gave purified title cis-II isomer, m.p. 93.5°–95° C.

The relative stereochemistry of the cis-I isomer was determined by X-ray crystallography.

The sodium salt of the cis-I isomer is prepared by dissolving 1 g. of cis-isomer in 25 ml. of water with 1 equivalent of 1N NaOH. The resulting solution is freeze dried to obtain the solid sodium salt.

EXAMPLE 7

2-(3-Cyclohexen-1-yl)-2-hydroxyacetonitrile

3-Cyclohexene-1-carbaldehyde (11.7 ml. 0.1 mole) and sodium bisulfite (15.5 g., 0.15 mole) were combined with 150 ml. of $H_2O$ and heated at 50°–60° C. for 2 hours. The mixture was cooled to 5° C. and added dropwise over 10 minutes to a cold solution of KCN (19.5 g., 0.3 mole) in 50 ml. $H_2O$. The mixture was warmed to 20° C., KCN (6.5 g., 0.1 mole) added as a solid, stirred for 10 minutes, and product extracted into 100 ml. ethyl acetate. The ethyl acetate extract was washed with brine and evaporated to yield title product as an oil, 8.5 g., Rf (5:1 hexane:ethyl acetate/5% $CH_3CO_2H$) 0.5.

EXAMPLE 8

2-(3-Cyclohexen-1-yl)-2-hydroxyacetamide

By the procedure of Example 3, title product of the preceding Example (6.2 g.) was reacted with KOH/$H_2O_2$ to form title product. After 35 minutes at 70° C., the reaction mixture was concentrated to 20 ml. and recovered by filtration, 0.74 g., m.p. 139°–141° C. The mother liquor was evaporated to dryness and triturated with 15 ml. of H₂O to yield a second crop of the title product, 0.32 g., m.p. 139°–141° C.

EXAMPLE 9

5-(3-Cyclohexen-1-yl)oxazolidine-2,4-dione

Title product of the preceding Example (1.2 g., 77 mmoles) was converted to crude title product according to Example 5, except reflux was continued for 3 hours. After evaporation to dryness, the residue was triturated with 15 ml. H₂O. Insoluble material (375 mg.) was removed by filtration. The filtrate was acidified with 6N HCl and extracted with 20 ml. ethyl acetate. The ethyl acetate layer was back-washed with H₂O and evaporated to an oil (0.6 g.). The oil was column chromatographed on 100 ml. silica gel with ethyl acetate as eluant and monitoring by tlc. Clean product fractions were combined and evaporated to yield purified title product, as a mixture of two racemic pair, 0.5 g., m.p. 83°–86° C., Rf (ethyl acetate) 0.9.

Anal. Calcd. for $C_9H_{11}O_3N$: C, 59.66; H, 6.12; N, 7.73; m/e 181. Found: C, 59.33; H, 5.93; N, 7.61; m/e 181.

EXAMPLE 10 cis-2-(2-Ethyl-3-cyclohexen-1-yl)-2-hydroxyacetonitrile

By the procedure of Example 1, the aldehyde of Preparation 3 (21.5 g.) was converted to title product, 22.8 g., containing trans-isomer by pnmr.

EXAMPLE 11 cis-2-(2-Ethyl-3-cyclohexen-1-yl)-2-hydroxyacetamide

By the procedure of Example 3, the 22.8 g. of title nitrile of the preceding Example was converted to present title product. An initial crop of product, 3.5 g., was recovered by filtration before ethyl acetate extraction. Recrystallization of the solids from acetone-hexane gave purified title product, 0.7 g., m.p. 156°–158° C. Additional title product (3.4 g.), contaminated with trans isomer was obtained from the ethyl acetate extracts and mother liquors.

EXAMPLE 12

5R*-(2S*-Ethyl-3-cyclohexen-1R*-yl)oxazolidine-2,4-dione (cis-I Isomer) and

5S*-(2S*-Ethyl-3-cyclohexen-1R*-yl)oxazolidine-2,4-dione (cis-II Isomer)

Purified title amide of the preceding Example (725 mg.) was reacted and isolated according to Example 6. The first crop (A) on crystallization from ether-hexane contained the title cis-I isomer as the major component, 168 mg., m.p. 135°–140° C. The second crop (B), 405 mg., m.p. 95°–98° C., was recrystallized from ether-hexane: 1st crop (C), 150 mg., m.p. 103°–106°; 2nd crop (D) 118 mg., m.p. 95°–98° C. containing title cis-II isomer as the major component. This Example was repeated on 3.4 g. of the same amide. The initial ether-hexane recrystallization gave four crops: (E), 115 mg., m.p. 155°–157° C.; (F), 43 mg. (m.p. 152°–154° C.); (G), 190 mg., m.p. 97°–101° C.; (H), 309 mg., m.p. 85°–95° C.

Crop A, 120 mg., was recrystallized from ether/hexane, to yield crop (J), m.p. 152°–154° C. Crops (F) and (J) were combined and recrystallized from ether-hexane to yield purified title cis-I isomer, 36 mg., m.p. 156.5°–157.5° C. Crop (G), 110 mg., recrystallized in like manner gave more purified cis-I isomer, 69 mg., m.p. 157°–158° C., pnmr includes 4.72 ppm, doublet, J=10.5.

Anal. Calcd. for $C_{11}H_{15}O_3N$: C, 63.14; H, 7.23; N, 6.69. Found: C, 62.63; H, 7.12; N, 6.64.

Combined crops (D) and (G), 305 mg. were recrystallized in like manner to yield crop (L), 191 mg., m.p. 103°–105° C. Combined crops (C) and (L), 340 mg., were recrystallized in like manner to yield purified cis-II isomer, 241 mg., m.p. 104.5°–106°, recrystallized once more for analysis, 166 mg., m.p. 105°–106.5° C.

Anal. Calcd. for $C_{11}H_{15}O_3N$: C, 63.14; H, 7.23; N, 6.69. Found: C, 63.07; H, 7.18; N, 6.74.

EXAMPLE 13

2-(6-Methyl-3-cyclohexen-1-yl)-2-hydroxyacetonitrile

By the procedure of Example 7, 6-methyl-3-cyclohexene-1-carbaldehyde, 9.3 g., 0.075 mole, was converted to present title product, oil, 7.5 g., m/e 151, Rf (5:1 hexane:ethyl acetate/5% $CH_3CO_2H$) 0.3.

EXAMPLE 14

2-(6-Methyl-3-cyclohexen-1-yl)-2-hydroxyacetamide

By the procedure of Example 3, title nitrile of the preceding Example (7.5 g.) was converted to present title product. After evaporation of the reaction mixture to dryness, the residue was triturated with 50 ml. of H₂O to yield title product as a white solid in two crops, 676 mg. and 657 mg., Rf (5:1 hexane:ethyl acetate/5% $CH_3CO_2H$) 0.25, contaminated with starting nitrile by tlc. Most of the latter was removed by trituration with hexane; thus the second crop gave purified title product, 572 mg.

EXAMPLE 15

5-(6-Methyl-3-cyclohexen-1-yl)oxazolidine-2,4-dione

By the procedure of Example 9, title amide (670 mg.) was converted to present title product as a solid mixture of racemates, 560 mg.

Anal. Calcd. for $C_{10}H_{13}O_3N$: C, 61.52; H, 6.71; N, 7.18; m/e 195. Found: C, 61.22; H, 6.69; N, 7.19; m/e 195.

EXAMPLE 16

2-(4-Methyl-3-cyclohexen-1-yl)-2-hydroxy acetonitrile

By the procedure of Example 1, 4-methyl-3-cyclohexene-1-carbaldehyde (16.1 g., 0.13 mole) was converted to title product as an oil, 13.6 g., m/e 151, Rf (5:1 hexane:ethyl acetate/5% $CH_3CO_2H$) 0.4.

EXAMPLE 17

2-(4-Methyl-3-cyclohexen-1-yl)-2-hydroxyacetamide

By the procedure of Example 14, title nitrile of the preceding Example (6.8 g., 0.045 mole) was converted to present title product. After the initial reflux subsided, the mixture was heated in an oil bath at 110°–120° C. for 0.5 hour. On evaporation of the reaction mixture to dryness, the residue was triturated in 80 ml. of water and title product recovered as a gummy solid by filtration, completely solidified by dissolving in acetone and re-evaporation, 553 mg., m/e 169, Rf (1:1 hexane:ethyl acetate/5% $CH_3CO_2H$) 0.5.

EXAMPLE 18

5-(4-Methyl-3-cyclohexen-1-yl)oxazolidine-2,4-dione

By the procedure of Example 6, the title amide of the preceding Example (500 mg.) was converted to column chromatographed title product as a mixture of two racemates, 353 mg., m.p. 60°–65° C. Recrystallization from 2 ml. ether/8 ml. hexane gave purified title product, 195 mg., m.p. 64.5°–66° C.

Anal. Calcd. for $C_{10}H_{13}O_3N$: C, 61.52; H, 6.71; N, 7.18; m/e 195. Found: C, 61.38; H, 6.93; N, 7.13; m/e 195.

By the same three step procedures of the preceding Examples, 5-methyl-3-cyclohexene-1-carbaldehyde is inverted to 5-(5-methyl-3-cyclohexen-1-yl)oxazolidine-2,4-dione.

EXAMPLE 19 endo- and exo-2-(Bicyclo[2.2.1]hept-5-en-2-yl)-2-hydroxyacetonitrile

By the procedure of Example 7, bicyclo[2.2.1]hept-5-ene-2-carbaldehyde (commercial 5-norbornene-2-carboxaldehyde, bp 60°–70°/12 mm.; $n_D^{20}$ 1.4883; endo/exo isomers unspecified; 25 g., 0.2 mole) was converted to title product as an oil, 10.3 g., Rf (1:1 hexane:ethyl acetate/ 5% acetic acid) 0.8.

EXAMPLE 20

2-(Bicyclo[2.2.1]hept-5-en-2-yl)-2-hydroxyacetamide

By the procedure of Example 3, title nitrile of the preceding Example (10.3 g., 0.069 mole) was converted to present title product as an oil, 5.4 g. The crude oil was purified by chromatography on silica gel. The column was first eluted with 1:2 hexane:ethyl acetate to remove unreacted starting material and then with ethyl acetate to obtain title product as a white solid, 2.8 g., m/e 167, Rf (1:1 hexane:ethyl acetate/5% acetic acid) 0.3.

EXAMPLE 21 endo- and exo-5-(Bicyclo[2.2.1]hept-5-en-2-yl)-oxazolidine-2,4-dione

By the procedure of Example 6, title amide of the preceding Example (2.7 g.; 0.016 mole) was converted to present title product isolated as a solid, 2.64 g., recrystallized from methanol/$H_2O$, 1.73 g. The latter (100 mg.) recrystallized from acetone-hexane gave almost quantitative recovery, m.p. 146°–149° C. The balance recrystallized from ether hexane gave the main batch of purified products, 1.02 g., m.p. 142°–146° C.

Anal. Calcd. for $C_{10}H_{11}O_3N$: C, 62.16; H, 5.74; N, 7.25; m/e 193. Found: C, 61.81; H, 5.53; N, 7.20; m/e 193.

Pnmr indicated the main product to be about 80% endo isomer and 20% exo isomer. A portion of this mixture (500 mg.) was dissolved in 10 ml. of hot isopropyl ether, concentrated to 7 ml. and allowed to stand at room temperature. Pure endo isomer crystallized, 190 mg., m.p. 153°–155° C.

EXAMPLE 22 endo- and exo-5-(Bicyclo[2.2.1]hept-2-yl)-oxazolidine-2,4-dione

Title product of the preceding Example (195 mg., 80% endo/20% exo) in 15 ml. absolute ethanol was hydrogenated at 40 psig over 70 mg. 5% Pd/C for 15 minutes. Catalyst was recovered by filtration. Evaporation of the filtrate to dryness gave title product, 160 mg., m.p. 134°–138° C.

Anal. Calcd. for $C_{10}H_{13}O_3N$: C, 61.51; H, 6.71; N, 7.18; m/e 195. Found: C, 61.23; H, 6.87; N, 7.54; m/e 195.

In the same manner, pure endo isomer of the preceding Example (185 mg.) in 20 ml. absolute ethanol over 50 mg. 5% Pd/C was converted the present pure endo isomer, 150 mg., m.p. 145°–146.5°.

Anal. Calcd. for $C_{10}H_3O_3N$: C, 61.51; H, 6.71; N, 7.18. Found: C, 61.04; H, 6.39; N, 7.10.

EXAMPLE 23

2-(Bicyclo[3.1.0]hex-2-en-6-yl)-2-hydroxyacetonitrile

By the procedure of Example 1, bicyclo[3.1.0]hex-2-ene-6-carbaldehyde (12.5 g., 0.12 mole) was converted to title product, isolated by extracting the reaction mixture with 150 ml. ethyl acetate; and back washing the organic layer 2×25 ml. $H_2O$, drying over $Na_2SO_4$ and evaporating to yield title product as an oil, 14.3 g., purified by column chromagraphy on 350 ml. silica gel with 1:1 hexane:ethyl acetate as eluant, re-isolated as a second oil, 9.82 g., m/e 135, Rf (5:1 hexane:ethyl acetate/5% $CH_3CO_2H$) 0.25, Rf (2:1 hexane: ethyl acetate)0.7.

EXAMPLE 24

2-(Bicyclo[3.1.0]hex-2-en-6-yl)-2-hydroxyacetamide

By the procedure of Example 3, title nitrile of the preceding Example (9.0 g., 0.067 mole) was converted to present title product, purified by column chromatography on 500 ml. silica gel with ethyl acetate as eluant, solid, 0.83 g., Rf (2:1 hexane:ethyl acetate) 0.35, m/e 153.

EXAMPLE 25

5-(Bicyclo[3.1.0]hex-2-en-6-yl)-oxazolidine-2,4-dione

By the procedure of Example 6, title amide of the preceding Example (0.8 g., 0.005 mole) was converted to present title product, initially isolated as a brown oil and then as a clear oil after chromatography, 0.45 g., Rf (1:1 hexane:ethyl acetate/5% $CH_3CO_2H$) 0.2.

The corresponding potassium salt is obtained by dissolving 250 mg. of title product with 7.5 ml. of water and 1 equivalent of 1N KOH. The salt is isolated by freeze drying.

EXAMPLE 26

5-(Bicyclo[3.1.0]hex-6-yl)oxazolidine-2,4-dione

By the procedure of Example 22, title product of the preceding Example (114 mg.) was converted to present title product, 98 mg. Colloidal carbon was removed by dissolving the product in acetone, filtering through diatomaceous earth and evaporating the filtrate to dryness. Recovery: 65 mg., m.p. 135°–141° C., pnmr includes proton signal at 4.60 ppm.

Anal. Calcd. for $C_9H_{13}O_3N.1/8H_2O$: C, 59.00; H, 6.14; N, 7.65. Found: C, 58.84; H, 5.96; N, 7.58.

EXAMPLE 27

2-(1-Methyl-3-cyclohexen-1-yl)-2-hydroxyacetonitrile

By the procedure of Example 1, the aldehyde of Preparation 4 (15.0 g., 0.12 mole) is converted to present title product. The reaction mixture was concentrated to near dryness, diluted with 125 ml. $H_2O$ and extracted 2×200 ml. ethyl acetate. The combined organic layers were back-washed 3×25 ml. H$_2$O, dried over Na$_2$SO$_4$ and evaporated to yield title product as an oil, 8.0 g., m/e 151, Rf (5:1 hexane:ethyl acetate/5% CH$_3$CO$_2$H) 0.5.

EXAMPLE 28

2-(1-Methyl-3-cyclohexen-1-yl)-2-hydroxyacetamide

By the procedure of Example 3, title nitrile (8.0 g. 0.053 mole) of the preceding Example was converted to present title product. The reaction mixture was evaporated to near dryness and diluted with 20 ml. H$_2$O. After stirring in an ice bath for 20 minutes, title product was recovered by filtration, dried at 50° C. in vacuo for 16 hours, 1.5 g., m.p. 102.5°–110° C., pnmr: 0.89 (CH$_3$), 1.2–2.47 (3×CH$_2$), 3.67 (CH), 4.72–5.42 (OH), 5.57 (CH=CH), 6.34–7.04 (NH$_2$) ppm.

EXAMPLE 29

5-(1-Methyl-3-cyclohexen-1-yl)oxazolidine-2,4-dione

Except that 1:1 hexane:ethyl acetate was used as eluant on chromatography, the procedure of Example 9 was used to convert title amide (1.4 g., 8.3 mmoles) of the preceding Example to present title product, clear oil, 1.4 g., m/e 195, Rf (1:1 hexane:ethyl acetate/5% CH$_3$CO$_2$H) 0.5.

Anal. Calcd. for C$_{10}$H$_{13}$O$_3$N: C, 61.52; H, 6.71; N, 7.18; O, 24.59. Found: C, 61.07; H, 6.38; N, 7.02; O, 24.46.

EXAMPLE 30

2-(2-Methyl-1-cyclohexen-1-yl)-2-hydroxyacetonitrile

2-Methyl-1-cyclohexene-1-carbaldehyde (3.7 g., 29.8 mmole), trimethylsilyl cyanide (4.7 ml., 1.25 equivalents) and 50 mg. of zinc iodide were stirred in 50 ml. of ether for 1.5 hours at room temperature. The reaction mixture was filtered over diatomaceous earth and the filtrate concentrated in vacuo. The residual trimethylsilyl ether was taken up in 50 ml. acetone and acidified with 5 ml. 6N HCl. The mixture was stirred for 3 hours at room temperature, diluted with 500 ml. of ether, and the aqueous layer separated and discarded. The organic layer was washed 1×50 ml. saturated NaHCO$_3$, dried over Na$_2$SO$_4$ and concentrated to an oil (3.2 g.). The oil was chromatographed on 100 ml. silica gel initially with 9:1, then 4:1, then 2:1 hexane:ethyl acetate and finally ethyl acetate as eluant. Product fractions were combined and evaporated to yield title product as an oil, 800 mg.

EXAMPLE 31

Ethyl 1-(2-Methyl-1-cyclohexen-1-yl)-1-hydroxymethanecarboximidate Hydrochloride Title product of the preceding Example (800 mg.) was dissolved in 10 ml. of saturated ethanolic HCl at 5° C. and maintained at 5°–10° C. for 2 hours. Evaporation to dryness and trituration with 10 ml. hexane gave title product as a gum (560 mg.).

EXAMPLE 32

5-(2-Methyl-1-cyclohexen-1-yl)oxazolidine-2,4-dione

Title product of the preceding Example (560 mg., 2.4 mmoles), tetrahydrofuran (50 ml.) and triethylamine (1.4 ml., 10 mmoles) were combined in an ice-water bath, and perfused with COCl$_2$ for 20 minutes. After flushing with N$_2$, the reaction mixture was poured into 100 ml. ice and water and extracted with 50 ml. ether. The organic layer was washed with water and concentrated to an oil (340 mg.). The oil was chromatographed on 50 ml. silica gel with 5:1 hexane:ethyl acetate/5% acetic acid as eluant. Title product was recovered as a yellow oil (240 mg.), crystallized by dissolving in 2 ml. of isopropyl ether and added hexane (2 ml.) to the haze point, 75 mg., m.p. 104°–106° C.

Anal. Calcd. for C$_{10}$H$_{13}$O$_3$N: C, 61.52; H, 6.71; N, 7.18. Found: C, 61.37; H, 6.90; N, 7.25.

EXAMPLE 33

2-(4-Methylenecyclohexan-1-yl)-2-trimethylsiloxyacetonitrile

A mixture of 4-methylenecyclohexane-1-carbaldehyde (12.3 g., 0.099 mole), trimethylsilyl cyanide (121 g., 0.12 mole) and zinc iodide (100 mg.) was stirred for 16 hours at room temperature. The reaction mixture was filtered over diatomaceous earth and the filtrate evaporated to yield title product (11.5 g.).

EXAMPLE 34

2-(4-Methylenecyclohexan-1-yl)-2-hydroxyacetamide

By the method of Example 3, noting unusually vigorous reaction when heat was first applied and some resultant loss in product, title product of the preceding Example (7.0 g., 31.3 mmole) was converted to present title product. Following the addition of NaHSO$_3$ (1 g.), the reaction mixture was partially concentrated, removing two crops of crude title product in the process. These crops were combined, taken up in acetone, filtered over diatomaceous earth and title product recovered by evaporation to solids, 490 mg., m.p. 127°–129° C.

EXAMPLE 35

5-(4-Methylenecyclohexan-1-yl)oxazolidine-2,4-dione

By the method of Example 5, title product of the preceding Example (460 mg., 2.7 mmole) was converted to present title product, an oil which crystallized on standing in the refrigerator (490 mg.). Recrystallization from CH$_2$Cl$_2$/hexane gave purified product, 295 mg., m.p. 63°–64° C.

Anal. Calcd. for C$_{10}$H$_{13}$NO$_3$: C, 61.52; H, 6.72; N, 7.18. Found: C, 61.14; H, 6.59; N, 7.20.

EXAMPLE 36

2-(6-Methyl-1-cyclohexen-1-yl)-2-trimethylsiloxyacetonitrile

By the method of Example 33, 6-methyl-1-cyclohexene-1-carbaldehyde (J. Org. Chem., 43:152, 1978, 4.6 g., 37 mmoles) was converted to present title product, isolated as an oil (10.3 g.).

EXAMPLE 37

Ethyl 1-(6-Methyl-1-cyclohexen-1-yl)-1-hydroxymethanecarboximidate Hydrochloride By the method of Example 31, title product of the preceding Example (10.3 g.) was converted to present title product (triturated with acetone rather than hexane), solid, 2.07 g. Evaporation of the acetone to dryness gave an additional 4.6 g. of title product as an oil.

EXAMPLE 38

5-(6-Methyl-1-cyclohexen-1-yl)oxazolidine-2,4-dione

By the method of Example 32, title product of the preceding Example (6.6 g., 28.6 mmoles) was converted to present title product. After quenching with ice and water, the product was extracted into ethyl acetate. The extract was back-washed with water and evaporated to an oil, 7.1 g. A portion (1.5 g.) was chromatographed as in Example 32, yielding purified title product as an oil, 390 mg., pnmr shows oxazolidinedione C.5 hydrogen as a doublet at delta 5.2 ppm.

Anal. Calcd. for $C_{10}H_{13}O_3N$: C, 61.52; H, 6.71; N, 7.18; m/e 195. Found: C, 61.07, H, 6.87; N, 7.46; m/e 195.

PREPARATION 1 cis-2-Methyl-3-cyclohexene-1-carbaldehyde

Method A 1,3-Pentadiene (7.64 g., 0.112 mole, 90% pure, mixed cis-trans isomers), acrolein (8.89 g., 0.159 mole) and hydroquinone (about 100 mg.) were dissolved in 125 ml. of ether at 0° C. Boron trifluoride etherate (8.94 g., 0.063 mole) in 20 ml. of ether, initially at 0° C. was added dropwise, with continued cooling, at a rate which kept the temperature in the range 10°–20° C. Following addition, the reaction mixture was stirred at room temperature for 30 minutes, washed in sequence 1×75 ml. $H_2O$, 1×120 ml. saturated $NaHCO_3$ and 1×50 ml. $H_2O$, dried over $Na_2SO_4$ and concentrated in vacuo at 25° C. or less to yield title product as a clear oil. Distillation (b.p. 80° C./18 mm.) gave purified title product (5.7 g.) Both the clear oil and the distilled product contained about 2% of the trans isomer on the basis of pnmr assay. Cis isomer shows TMS/delta 9.8 ppm while trans epimer shows TMS/delta 9.7 ppm.

Method B 1,3-Pentadiene (90%, mixed isomers, 1.36 g., 0.02 mole), acrolein (1.40 g., 0.025 mole) and about 20 mg. of hydroquinone were dissolved in 25 ml. $CH_2Cl_2$ at 0° C. Stannic chloride (2.60 g., 10 mmole) in 5 ml. $CH_2Cl_2$ was added dropwise, maintaining the temperature in the range 5°–25° C. After addition was complete, the reaction mixture was stirred for 30 minutes at room temperature, diluted with 50 ml. $H_2O$ (initially added slowly) and the layers separated. The aqueous layer wash washed 2×30 ml. $CH_2Cl_2$. The organic layers were combined, dried over $Na_2SO_4$, and concentrated in vacuo to yield title product as an oil, almost free of trans isomer by pnmr assay. Distillation (bp 60°/12 mm.) led to title product (2 g.), isomerized to trans isomer to the extent of about 15%. Isomerization is avoided by incorporating a $NaHCO_3$ wash into the prior isolation, as in Method A.

Title product can also be prepared according to methods detailed by Berson et al., J. Am. Chem. Soc., 98, 5937 (1976).

PREPARATION 2 trans-2-Methyl-3-cyclohexene-1-carbaldehyde

Method A 1,3-Pentadiene (18 g., 0.264 mole, 90%, mixture of isomers), acrolein (16.3 g., 0.29 mole) were refluxed for 24 hours, using an oil bath at 65° C. Evaporation in vacuo gave 15 g., of a 20 to 80 mixture of desired title product (trans isomer) to corresponding cis epimer.

Such a 20:80 trans:cis mixture (31 g.) was combined with 40 ml. acetic acid and 15 ml. 2N $H_2SO_4$ and heated at 80°–83° C. for 3 hours. The reaction mixture was cooled to room temperature, diluted with 200 ml. $H_2O$, and the resulting brown oil separated. The oil was dissolved in 50 ml. hexane, washed with 25 ml. $H_2O$ and the hexane removed by evaporation in vacuo. Distillation gave 26 g. of title trans product containing 15% cis isomer by pnmr assay bp 52° C./12 mm.

Method B

A mixture of 1,3-pentadiene (90%, mixed isomers, 2.3 ml., 0.02 mole), acrolein (1.7 ml., 0.025 mole), tetrahydrofuran (15 ml.), hydroquinone (about 20 mg.) and borontrifluoride etherate (1.25 ml., 0.01 mole) was refluxed under $N_2$. Formation of cis isomer and its subsequent conversion to trans isomer was followed by pnmr assay. At 30 minutes, the cis/trans ratio was 85/15; at 6 hours it was 17/83 and at 14 hours 15/85. Title product was recovered according to Preparation 1, Method A.

Alternatively, title product is prepared according to Berson et al., loc. cit.

PREPARATION 3 cis-2-Ethyl-3-cyclohexene-1-carbaldehyde

A mixture of 1,3-hexadiene (cis/trans mixture, 20 g., 0.24 mole), acrolein (18 ml., 0.27 mole) and hydroquinone (50 mg.) was heated at 70°–75° C. for 22 hours. Distillation in vacuo gave purified title product (21.7 g.; b.p. 90° C./12–15 mm.; 78% cis, 22% trans by pnmr assay).

PREPARATION 4

1-Methyl-3-cyclohexene-1-carbaldehyde

Methacolein (27.3 ml., 0.33 mole) was combined with 165 ml. benzene and cooled to 3° C. Stannic chloride (5.4 ml., 0.046 mole) in 16.5 ml. of benzene was added dropwise over 5–10 minutes, the temperature rising to 12° C. 1,3-Butadiene gas was then perfused through the reaction mixture over 3 hours, maintaining the temperature 20°–30° C., initially by occasional cooling with an ice-water bath. The reaction mixture was quenched into 100 ml. of ice and water. The organic layer was separated, washed in sequence 1×25 ml. dilute HCl, 2×25 ml. 5% NaCl and 1×25 ml. saturated $NaHCO_3$, dried over $Na_2SO_4$, filtered, evaporated to dryness and the residue distilled in vacuo to yield title product, 20.4 g., b.p. 49.5°/11 mm., m/e 124, pnmr: 1.09 ($CH_3$), 1.23–2.63 (3×$CH_2$), 5.69 ($CH=CH$), 9.57 ($CHO$) ppm.

PREPARATION 5

2-Hydroxymethylenecyclohexanone

A mixture of 50% sodium hydride dispersion in oil (24 g., 0.5 mole) and absolute ethanol (2.5 ml., 43 mmole) in 1 liter ether were stirred under $N_2$ at 0° C. To the cold solution, cyclohexanone (51.5 ml., 0.5 mole) in ethyl formate (60 ml., 0.75 mole) was added dropwise at 0°–5° C. The cooling bath was removed. The temperature rose to the boiling point of ether over 30 minutes. The reaction mixture was recooled, warmed gradually to room temperature over 6 hours and finally stirred for an additional 16 hours. Ether lost by evaporation was replaced by diluting to 1 liter with fresh ether. Ethanol (12.5 ml.) was added and stirring continued for 1 hour.

The mixture was extracted with 125 ml. water in two portions. The combined aqueous extracts were washed 1×50 ml. ether, acidified with 82 ml. 6N HCl, and extracted 2×150 ml. with fresh ether. The acid ether extracts were combined, washed 1×25 ml. brine, dried over Na₂SO₄, evaporated to an oil and distilled to yield title product, 44 g., b.p. 92°–98°/15–20 mm.

PREPARATION 6

2-(Isopropoxymethylene)cyclohexanone

Title product of the preceding Preparation (24 g.) in 160 ml. isopropanol and 110 ml. of benzene containing 100 mg. of p-toluenesulfonic acid was distilled azeotropically using a 6 inch Vigreaux column. After 150 ml. distillate was recovered, 50 ml. isopropanol and 50 ml. benzene were added to the pot and 100 ml. addition distillate collected. The pot residue was cooled, stirred with 25 g. K₂CO₃ for 30 minutes, filtered and the filtrate concentrated to an oil. Title product was purified by distillation, 16 g., b.p. 72°–74° C./0.3 mm.

PREPARATION 7

2-Methyl-1-cyclohexene-1-carbaldehyde

To 118 ml. (190 mmole) of 1.6M methyllithium in tetrahydrofuran, cooled under N₂ to −78° C., was added over 30 minutes title product of the preceding Preparation (16 g., 95 mmole) in 100 ml. ether. After 30 minutes at −78° C., the reaction mixture was warmed slowly to room temperature, stirred for 1 hour, quenched by slowly adding 50 ml. 1N HCl, stirred 15 minutes, poured into 500 ml. water and extracted 3×150 ml. ether. The combined ether extracts were washed 1×50 ml. H₂O, 1×50 ml. saturated NaHCO₃, dried over Na₂SO₄, concentrated to an oil, taken up in 300 ml. acetone, cooled to 0° C. and treated dropwise with Jones reagent until a faint orange color persisted (about 10 ml.). The solution was warmed to room temperature, stirred 15 minutes, diluted with 200 ml. of water, and concentrated in vacuo to remove acetone. The concentrate was extracted 3×100 ml. ether. The ether extracts were combined, washed 1×50 ml. water and 1×50 ml. saturated NaHCO₃, dried over Na₂SO₄; concentrated to an oil and title product recovered by distillation, 6.4 g., b.p. 58°–62°/0.2 mm., pnmr (CCl₄) includes aldehyde proton peak at delta 9.9–10 ppm.

PREPARATION 8

4-Methylenecyclohexane-1-carbaldehyde

To pydridinium dichromate (223 g., 0.59 mole) in 1 liter CH₂Cl₂, stirring under N₂, was added dropwise 4-methylene-1-cyclohexanemethanol (50 g., 0.40 mole) in 75 ml. CH₂Cl₂ over a few minutes. After stirring for 21 hours at room temperature, the reaction mixture was heated at 60° C. for 24 hours. The reaction mixture was cooled, diluted with 400 ml. ether and decanted from solids. The solids were slurried with 400 ml. of fresh ether and decanted. The combined organic decants were filtered over fluorasil and diatomaceous earth and the filtrate concentrated in vacuo to an oil (41 g.) and distilled to yield title product, 13.6 g., b.p. 82°–90°/15–20 mm.

I claim:

1. A compound of the formula

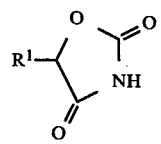

or a pharmaceutically-acceptable cationic salt thereof; wherein R¹ is a hydrocarbon radical having a molecular formula which is either $C_nH_{2n-3}$ (having either two carbocyclic rings or one carbocyclic ring and one double bond) or $C_nH_{2n-5}$ (having two carbocyclic rings and one double bond), wherein n is an integer of value 5 to 9, which is further characterized by having within its structure:
   (a) at least one of said rings comprising five or more carbon atoms; and
   (b) up to one substituent (C₁–C₃)alkyl or (C₁–C₃) alkylidene group.

2. A compound of claim 1 wherein R¹ is of the formula $C_nH_{2n-5}$.

3. A compound of claim 2 wherein R¹ contains at least one 6-membered carbocyclic ring.

4. A compound of claim 3 which is the exo-form or the endo-form of 5-(bicyclo[2.2.1]hept-5-en-2-yl)oxaxolidine-2,4-dione.

5. The compound of claim 4 which is endo-5-(bicyclo[2.2.1]hept-5-en-2-yl)oxazolidine-2,4-dione.

6. The compound of claim 2 which is 5-(bicyclo[3.1.0]hex-2-en-6-yl)oxazolidine-2,4-dione.

7. A compound of claim 1 wherein R¹ is of the formula $C_nH_{2n-3}$.

8. A compound of claim 7 wherein R¹ contains two carbocyclic rings.

9. A compound of claim 8 wherein at least one of the carbocyclic rings is six membered.

10. A compound of claim 9 which is the exo-form or the endo-form of 5-(bicyclo[2.2.1]hept-2-yl)oxazolidine-2,4-dione.

11. The compound of claim 10 which is endo-5-(bicyclo[2.2.1]hept-2-yl)oxazolidine-2,4-dione.

12. The compound of claim 8 which is 5-(bicyclo[3.1.0]hex-2-yl)oxazolidine-2,4-dione.

13. A compound of claim 7 where R¹ contains one carbocyclic ring and one double bond.

14. A compound of claim 13 wherein the carbocyclic ring is 6-membered.

15. A compound of claim 14 wherein R¹ is 3-cyclohexen-1-yl, optionally substituted at the 2-, 4- or 6-position with a methyl or an ethyl group.

16. The compounds of claim 15 wherein R¹ is 3-cyclohexen-1-yl.

17. The compounds of claim 15 wherein R¹ is 4-methyl-3-cyclohexen-1-yl.

18. The compounds of claim 15 wherein R¹ is 6-methyl-3-cyclohexene-1-yl.

19. The compounds of claim 15 wherein R¹ is 2-ethyl-3-cyclohexen-1-yl or 2-methyl-3-cyclohexen-1-yl.

20. The compounds of claim 19 wherein the 1,2-hydrogens on the cyclohexene ring bear a cis-relationship.

21. The racemic compound of claim 20 which is 5R*-(2S*-methyl-3-cyclohexen-1R*-yl)oxazolidine-2,4-dione.

22. A pharmaceutical composition suitable for use in lowering the blood glucose in a hyperglycemic mammal which comprises a pharmaceutically acceptable carrier and a blood glucose lowering amount of a compound of claim 1.

23. A method of lowering the blood glucose in a hyperglycemic mammal which comprises administering a blood glucose lowering amount of a compound of a compound of claim 1.

* * * * *